May 4, 1948. E. E. MARSH Plant Pat. 797
CLIMBING ROSE PLANT
Filed Nov. 15, 1946
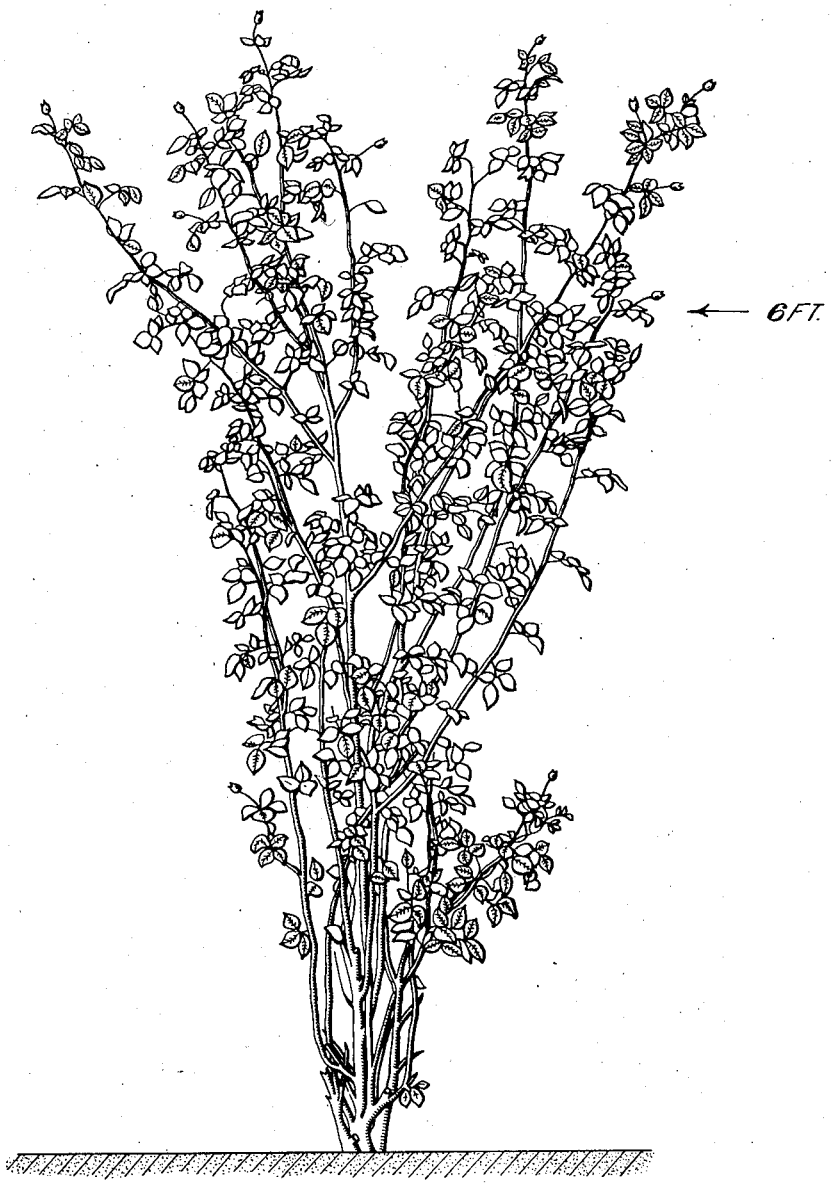
Inventor
Edward E. Marsh
By Lyon & Lyon
Attorney Patented May 4, 1948

Plant Pat. 797

UNITED STATES PATENT OFFICE

797

CLIMBING ROSE PLANT

Edward E. Marsh, Pasadena, Calif.

Application November 15, 1946, Serial No. 712,811

1 Claim. (Cl. 47—61)

This invention relates to a new and distinct variety of hybrid tea rose plant originating as a sport found on a bush plant of the well known "Pasadena Tournament" rose, Patent No. 578, issued April 27, 1943.

The dominating characteristics of this new rose are its strong and vigorous climbing form and its profuse blossoming and having no apparent tendency to revert to bush form when propagated by budding.

The single figure of the drawing illustrates a plant of this variety.

As regards its other characteristics, particularly color and form, no differences are notable as it follows the characteristic form of the "Pasadena Tournament" rose of the bush variety.

As is true of the bush "Pasadena Tournament" plants, the climbing plant of this invention produces velvety carmine buds of velvety texture and sheen wherein each bud has one long sepal and the plant is further characterized in that it has no thorns and its flowers are of long-lasting qualities. The rosebud develops similar to the common variety of Cecil Brunner rose but is of longer size. The rose is smaller in size than the commonly known "Paul Scarlet." The leaf structure is very similar to the leaf structure of the Cecil Brunner rose except as to the double leaf formation.

In each respect of color, foliage, budding and bloom the climbing rose plant of this invention truly follows the bush variety of the "Pasadena Tournament" hybrid tea rose bush plant defined in the Plant Patent No. 578, hereinabove referred to.

This sport and its characteristics were observed, and its propagation was determined by budding at Altadena, California, where the rose and the climbing rose reproduced by budding were grown outdoors.

What I claim is:

A new and distinct variety of hybrid tea rose plant, characterized as to novelty by its strong and vigorous climbing habit and the habit of producing profuse flowers in greater quantity than can be found on its bush parent, substantially as described.

EDWARD E. MARSH.